(12) United States Patent
Filippov et al.

(10) Patent No.: US 7,794,988 B2
(45) Date of Patent: Sep. 14, 2010

(54) **METHOD FOR PRODUCING AN L-AMINO ACID USING A BACTERIUM OF THE *ENTEROBACTERIACEAE* FAMILY WITH ATTENUATED EXPRESSION OF THE *RSPAB* OPERON**

(75) Inventors: Dmitriy Vladimirovich Filippov, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/345,971

(22) Filed: Dec. 30, 2008

(65) Prior Publication Data

US 2009/0170169 A1  Jul. 2, 2009

Related U.S. Application Data

(63) Continuation of application No. PCT/JP2007/063618, filed on Jul. 2, 2007.

(30) Foreign Application Priority Data

Jul. 4, 2006  (RU)  ............... 2006123752

(51) Int. Cl.
  *C12P 13/04*  (2006.01)
  *C12N 9/00*  (2006.01)
  *C12N 1/20*  (2006.01)
  *C12N 15/00*  (2006.01)
  *C07H 21/04*  (2006.01)

(52) U.S. Cl. ............... 435/106; 435/107; 435/183; 435/252.3; 435/320.1; 536/23.2

(58) Field of Classification Search ............... None
See application file for complete search history.

(56) References Cited

U.S. PATENT DOCUMENTS

| | | | |
|---|---|---|---|
| 4,278,765 A | 7/1981 | Debabov et al. |
| 4,346,170 A | 8/1982 | Sano et al. |
| 5,175,107 A | 12/1992 | Debabov et al. |
| 5,661,012 A | 8/1997 | Sano et al. |
| 5,688,671 A | 11/1997 | Sugimoto et al. |
| 5,932,453 A | 8/1999 | Kikuchi et al. |
| 6,040,160 A | 3/2000 | Kojima et al. |
| 6,132,999 A | 10/2000 | Debabov et al. |
| 6,303,348 B1 | 10/2001 | Livshits et al. |
| 6,319,696 B1 | 11/2001 | Kishino et al. |
| 7,138,266 B2 | 11/2006 | Debabov et al. |
| 7,186,531 B2 | 3/2007 | Akhverdian et al. |
| 7,259,003 B2 | 8/2007 | Livshits et al. |
| 7,312,058 B2 | 12/2007 | Kashiwagi et al. |
| 7,381,548 B2 | 6/2008 | Sheremet'eva et al. |
| 7,422,880 B2 | 9/2008 | Rybak et al. |
| 7,476,531 B2 | 1/2009 | Tabolina et al. |
| 2002/0110876 A1 | 8/2002 | Miyata et al. |
| 2004/0132165 A1 | 7/2004 | Akhverdian et al. |
| 2005/0214911 A1 | 9/2005 | Marchenko et al. |
| 2005/0239177 A1 | 10/2005 | Livshits et al. |
| 2006/0088919 A1 | 4/2006 | Rybak et al. |
| 2006/0216796 A1 | 9/2006 | Hashiguchi et al. |
| 2007/0004014 A1 | 1/2007 | Tsuji et al. |
| 2008/0113416 A1 | 5/2008 | Filippov et al. |
| 2008/0153138 A1 | 6/2008 | Livshits et al. |
| 2008/0261278 A1 | 10/2008 | Tabolina et al. |
| 2008/0261279 A1 | 10/2008 | Tabolina et al. |

FOREIGN PATENT DOCUMENTS

WO  WO95/16042  6/1995
WO  WO2008/004683  1/2008

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Huisman, G. W., et al., "Sensing Starvation: a Homoserine Lactone-Dependent Signaling Pathway in *Escherichia coli*," Science 1994;265(5171):537-539.
Schneider, D., et al., "Characterization of *spaA*, a *Streptomyces coelicolor* gene homologous to a gene involved in sensing starvation in *Escherichia coli*," Gene 1996;177:243-251.
International Search Report and Written Opinion of the International Searching Authority for PCT Patent App. No. PCT/JP2007/063618 (Oct. 18, 2007).
International Preliminary Report on Patentability for PCT Patent App. No. PCT/JP2007/063618 (Jan. 15, 2009).
Aronson, B. D., et al., "The Primary Structure of *Escherichia coli* L-Threonine Dehydrogenase," J. Biol. Chem. 1989;264(9):5226-5232.
Ikegami, M., et al., "The Collagen-like Region of Surfactant Protein A (SP-A) Is Required for Correction of Surfactant Structural and Functional Defects in the SP-A Null Mouse," J. Biol. Chem. 2001;276(42):38542-38548.
U.S. Appl. No. 11/830,961, filed Jul. 31, 2007, Filippov et al.
U.S. Appl. No. 11/849,415, filed Sep. 4, 2007, Filippov et al.
U.S. Appl. No. 11/849,403, filed Sep. 4, 2007, Rybak et al.
U.S. Appl. No. 11/934,890, filed Nov. 5, 2007, Filippov et al.
U.S. Appl. No. 12/017,379, filed Jan. 22, 2008, Rybak et al.
U.S. Appl. No. 61/031,834, filed Feb. 27, 2008, Samsonov et al.
U.S. Appl. No. 61/053,704, filed May 16, 2008, Rybak et al.
U.S. Appl. No. 12/125,988, filed May 23, 2008, Filippov et al.
U.S. Appl. No. 12/212,743, filed Sep. 18, 2008, Rybak et al.
U.S. Appl. No. 12/253,415, filed Oct. 17, 2008, Filippov et al.
U.S. Appl. No. 12/323,893, filed Nov. 26, 2008, Filippov et al.
U.S. Appl. No. 12/349,743, filed Jan. 7, 2009, Marchenko et al.

* cited by examiner

*Primary Examiner*—Christian L Fronda
(74) *Attorney, Agent, or Firm*—Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of the rspAB operon.

5 Claims, 2 Drawing Sheets

US 7,794,988 B2

METHOD FOR PRODUCING AN L-AMINO ACID USING A BACTERIUM OF THE ENTEROBACTERIACEAE FAMILY WITH ATTENUATED EXPRESSION OF THE RSPAB OPERON

This application is a continuation of PCT/JP2007/063618, filed Jul. 2, 2007. This application also claims priority under 35 U.S.C. §119 to Russian Patent Application No. 2006123752, filed on Jul. 4, 2006. Each of these documents is incorporated in their entireties by reference. The Sequence Listing in electronic format filed herewith is also hereby incorporated by reference in its entirety (File Name: US-341_Seq_List; File Size: 18 KB; Date Created: Dec. 30, 2008).

BACKGROUND OF THE INVENTION

1. Field of the Invention

The present invention relates to the microbiological industry, and specifically to a method for producing an L-amino acid using a bacterium of the Enterobacteriaceae family which has been modified to attenuate expression of the rspAB operon.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042, or U.S. Pat. Nos. 4,346,170, 5,661,012, and 6,040,160).

Another way to enhance L-amino acid production yields is to attenuate expression of a gene, or several genes, involved in degradation of the target L-amino acid, genes diverting the precursors of the target L-amino acid from the L-amino acid biosynthetic pathway, genes involved in the redistribution of carbon, nitrogen, and phosphate fluxes, and genes coding for toxins etc.

When the nutrient suppy becomes insufficient, many bacteria differentiate and become resistant to environmental stresses. For *Escherichia coli*, this process is mediated by the sigma S subunit of RNA polymerase. Expression of sigma S is induced by homoserine lactone, a metabolite synthesized from the intermediates in threonine biosynthesis. Homoserine lactone-dependent synthesis of sigma S was prevented by overexpression of the protein RspA. The function of homoserine lactone derivatives in many cell density-dependent phenomena and the similarity of RspA to a *Streptomyces ambofaciens* protein suggest that synthesis of homoserine lactone may be a general signal of starvation (G. W. Huisman and R. Kolter, Science, 265:537-539 (1994)).

rspB is likely to encode a catabolic enzyme because its gene product RspB is 38% identical to threonine dehydrogenase from *E. coli* (G. W. Huisman and R. Kolter, Science, 265:537-539 (1994), B. D. Aronson et. al., J. Biol. Chem., 264:5226-32 (1989)).

The genes rspA and rspB form an operon. This is based on data which shows that transposon insertion into rspA abolishes rspB expression (G. W. Huisman and R. Kolter, Science, 265:537-539 (1994)).

But currently, there are no reports of attenuating expression of the rspAB operon for the purpose of producing L-amino acids.

SUMMARY OF THE INVENTION

Objects of the present invention include enhancing the productivity of L-amino acid-producing strains and providing a method for producing L-amino acids using these strains.

The above objects were achieved by finding that attenuating expression of the rspAB operon can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family which has an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of the rspAB operon.

It is a further aspect of the present invention to provide the bacterium as described above, wherein the expression of the rspAB operon is attenuated by inactivation of the entire rspAB operon.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide a method for producing an L-amino acid comprising:
cultivating the bacterium as described above in a medium, and
collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DETAILED DESCRIPTION OF THE PREFERRED EMBODIMENTS

1. Bacterium of the Present Invention

Figure 1:
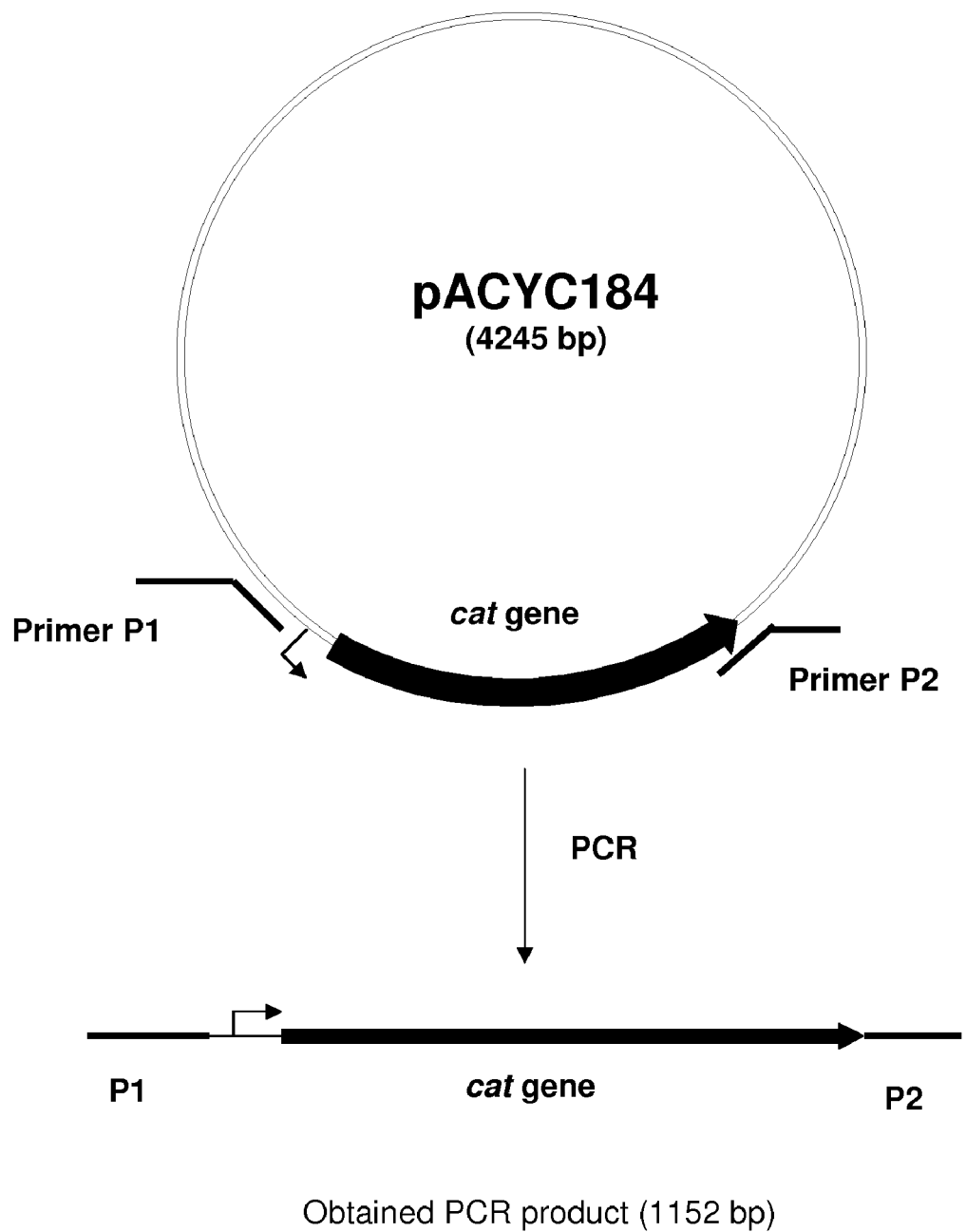
FIG. 1 shows the relative positions of primers P1 and P2 on plasmid pACYC184, which is used for amplification of the cat gene.

The bacterium of the present invention is an L-amino acid-producing bacterium of the Enterobacteriaceae family, wherein the bacterium has been modified to attenuate expression of the rspAB operon.

"L-amino acid-producing bacterium" means a bacterium which has an ability to produce and secrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of the bacterium, for example, *E. coli*, such as *E. coli* K-12, and preferably means that the bacterium is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae family according to the taxonomy used by the NCBI (National Center for Biotechnology Information) database (http://www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the rspAB operon" means that the bacterium has been modified in such a way that the modified bacterium contains reduced amounts of the RspA and RspB proteins as compared with an unmodified bacterium, or the modified bacterium is unable to synthesize the RspA and RspB.

The phrase "inactivation of the rspAB operon" means that the modified genes encode completely inactive proteins. It is also possible that the modified DNA region is unable to naturally express the genes due to a deletion of the gene cluster, shifting of the reading frame of the gene, introduction of missense/nonsense mutation(s), or modification of an adjacent region of the gene, including sequences controlling gene expression, such as promoter(s), enhancer(s), attenuator(s), ribosome-binding site(s), etc.

The presence or absence of the rspAB operon on the chromosome of a bacterium can be detected by well-known methods, including PCR, Southern blotting, and the like. In addition, the levels of expression of genes can be estimated by measuring the amounts of mRNAs transcribed from the genes using various well-known methods, including Northern blotting, quantitative RT-PCR, and the like. The amounts or molecular weights of the proteins encoded by the genes can be measured by well-known methods, including SDS-PAGE followed by immunoblotting assay (Western blotting analysis), and the like. The rspA gene encodes the RspA protein (synonym-B1581). The rspB gene encodes the RspB protein (synonym-B 1580). Both the rspA and rspB genes are located in the rspAB operon. The rspAB operon of *E. coli* (nucleotides complementary to nucleotides 1,651,951 to 1,653,165 and 1,650,920 to 1,651,939 for rspA and rspB, respectively, in the GenBank accession number NC_000913.2; gi:16129539 and gi:16129538 for rspA and rspB, respectively) is located between the intQ gene and the ynfA ORF on the *E. coli* K-12 chromosome. The nucleotide sequence of the rspA gene and the encoded RspA amino acid sequence are shown in SEQ ID NO: 1 and SEQ ID NO: 2, respectively. The nucleotide sequence of the rspB gene and the encoded RspB amino acid sequence are shown in SEQ ID NO: 3 and SEQ ID NO: 4, respectively.

Since there may be some differences in DNA sequences between the genera or strains of the Enterobacteriaceae family, the rspAB operon to be inactivated on the chromosome is not limited to the genes shown in SEQ ID NO: 1 and SEQ ID NO: 3 but may include genes homologous to SEQ ID NO: 1 and SEQ ID NO: 3 which encode variant proteins of the RspA and RspB proteins. The phrase "variant proteins" means proteins which have changes in the sequences, whether they are deletions, insertions, additions, or substitutions of amino acids. The number of changes in the variant proteins depends on the position in the three dimensional structure of the protein or the type of amino acid residues. It may be 1 to 30, preferably 1 to 15, and more preferably 1 to 5 in SEQ ID NO: 2 and SEQ ID NO: 4. These changes in the variants are conservative mutations that preserve the function of the protein. In other words, these changes in the variants can occur in regions of the protein which are not critical for the three dimensional structure of the protein. This is because some amino acids have high homology to one another so the three dimensional structure is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Substitutions, deletions, insertions, additions, or inversions and the like of the amino acids described above include naturally occurred mutations (mutant or variant) depending on differences in species, or individual differences of microorganisms that retain the rspA or rspB gene. Such a gene can be obtained by modifying the nucleotide sequence shown in SEQ ID NO: 1 or 3 using, for example, site-directed mutagenesis, so that the site-specific amino acid residue in the protein encoded includes substitutions, deletions, insertions, or additions.

Moreover, the protein variants encoded by the genes rspA and rspB may be ones which have homologies of not less than 80%, preferably not less than 90%, and most preferably not less than 95%, with respect to the entire amino acid sequence shown in SEQ ID NO: 2 and SEQ ID NO: 4, respectively.

Homology between two amino acid sequences can be determined using the well-known methods, for example, the computer program BLAST 2.0, which calculates three parameters: score, identity and similarity.

Moreover, the genes rspA and rspB may be variants which hybridize under stringent conditions with the nucleotide sequence shown in SEQ ID NO: 1 and SEQ ID NO: 3 or probes which can be prepared from the nucleotide sequences, respectively. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C.

Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, in this specific case, it may be about 100 bp to 1 kbp.

Expression of the rspAB operon can be attenuated by introducing mutations into the genes. Such a mutation on the gene can be replacement of one base or more to cause amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the rspAB operon can also be attenuated by modifying expression regulating sequences such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and the bacterium to be modified is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000), WO2005/010175), or by methods employing a plasmid containing a temperature-sensitive replication control region (Proc. Natl. Acad. Sci., USA, 97, 12, p 6640-6645 (2000), U.S. Pat. Nos. 6,303,383 and 5,616,480). Furthermore, the introduction of a site-specific mutation by gene replacement using homologous recombination as set forth above can also be performed by using a plasmid lacking the ability to replicate in the host.

Expression of the gene can also be attenuated by insertion of a transposon or an IS factor into the coding region of the gene (U.S. Pat. No. 5,175,107), or by conventional methods, such as mutagenesis treatment with UV irradiation or nitrosoguanidine (N-methyl-N'-nitro-N-nitrosoguanidine).

Inactivation of the gene can also be performed by conventional methods, such as by mutagenesis with UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45), also called "Red-driven integration".

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

The bacteria to be modified to attenuate expression of the rspAB operon may be bacteria which are able to produce either an aromatic or a non-aromatic L-amino acids.

The bacterium can be obtained by attenuating expression of the rspAB operon in a bacterium which inherently has the ability to produce L-amino acids. Alternatively, the bacterium can be obtained by imparting the ability to produce L-amino acids to a bacterium already having attenuated expression of the rspAB operon.

L-Threonine-Producing Bacteria

Examples of parent strains which can be used to derive the L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene in this strain has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow 1, Dorozhny proezd 1) on Apr. 7, 1987 under the accession number VKPM B-3996.

*E. coli* VKPM B-5318 (EP 0593792B) also may be used as a parent strain to derive L-threonine-producing bacteria of the present invention. The strain B-5318 is prototrophic with regard to isoleucine, and a temperature-sensitive lambda-phage C1 repressor and PR promoter replace the regulatory region of the threonine operon in the plasmid pVIC40 harbored by the strain. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes:
- the mutant thrA gene which codes for aspartokinase-homoserine dehydrogenase I resistant to feed back inhibition by threonine;
- the thrB gene which codes for homoserine kinase;
- the thrC gene which codes for threonine synthase;
- the rhtA gene which codes for a putative transmembrane protein;
- the asd gene which codes for aspartate-β-semialdehyde dehydrogenase; and
- the aspC gene which codes for aspartate aminotransferase (aspartate transaminase);

The thrA gene which encodes aspartokinase-homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is removed from the operon (WO2005/049808, WO2003/097839).

A mutant thrA gene which codes for aspartokinase-homoserine dehydrogenase I resistant to feed back inhibition by threonine, as well as the thrB and thrC genes can be obtained as one operon from the well-known plasmid pVIC40, which is present in the threonine producing *E. coli* strain VKPM B-3996. Plasmid pVIC40 is described in detail in U.S. Pat. No. 5,705,371.

The rhtA gene is located at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181), and is located between the pexB and ompX genes. The DNA sequence expressing a protein encoded by the ORF1 has been designated the rhtA gene (rht: resistance to homoserine and threonine). Also, it is known that the rhtA23 mutation is an A-for-G substitution at position—1 with respect to the ATG start codon (ABSTRACTS of the 17$^{th}$ International Congress of Biochemistry and Molecular Biology in conjugation with the Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria include, but are not limited to, strains belonging to the genus Escherichia, such as E. coli JM15 which is transformed with different cysE alleles coding for feedback-resistant serine acetyltransferases (U.S. Pat. No. 6,218,168, Russian patent application 2003121601); E. coli W3110 which over-expresses genes which encode proteins suitable for secreting substances toxic for cells (U.S. Pat. No. 5,972,663); E. coli strains having lowered cysteine desulfohydrase activity (JP11155571A2); E. coli W3110 with increased activity of a positive transcriptional regulator for cysteine regulon encoded by the cysB gene (WO0127307A1), and the like.

L-Leucine-Producing Bacteria

Examples of parent strains which can be used to derive L-leucine-producing bacteria include, but are not limited to, strains belonging to the genus Escherichia, such as E. coli strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); E. coli strains obtained by the genetic engineering methods such as those described in WO96/06926; E. coli H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase which is not subject to feedback inhibition by L-leucine (U.S. Pat. No. 6,403,342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains which can be used to derive L-histidine-producing bacteria include, but are not limited to, strains belonging to the genus Escherichia, such as E. coli strain 24 (VKPM B-5945, RU2003677), E. coli strain 80 (VKPM B-7270, RU2119536), E. coli NRRL B-12116-B12121 (U.S. Pat. No. 4,388,405), E. coli H-9342 (FERM BP-6675) and H-9343 (FERM BP-6676) (U.S. Pat. No. 6,344,347), E. coli H-9341 (FERM BP-6674) (EP1085087), E. coli AI80/pFM201 (U.S. Pat. No. 6,258,554), and the like.

Examples of parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation into any of these genes which imparts resistance to the feedback inhibition into enzymes encoded by the genes (Russian Patent Nos. 2003677 and 2119536).

Specific examples of strains having an L-histidine-producing ability include E. coli FERM-P-5038 and 5048 which have been transformed with a vector carrying a DNA encoding an L-histidine-biosynthetic enzyme (JP 56-005099 A), E. coli strains transformed with rht, which encodes an amino acid-exporter (EP1016710A), E. coli 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains which can be used to derive L-glutamic acid-producing bacteria include, but are not limited to, strains belonging to the genus Escherichia, such as E. coli VL334thrC$^+$ (EP 1172433). E. coli VL334 (VKPM B-1641) is an L-isoleucine and L-threonine auxotrophic strain having mutations in the thrC and ilvA genes (U.S. Pat. No. 4,278,765). A wild-type allele of the thrC gene was transferred using general transduction with a bacteriophage P1 which was grown on wild-type E. coli K12 (VKPM B-7) cells. As a result, an L-isoleucine auxotrophic strain VL334thrC$^+$ (VKPM B-8961), which is able to produce L-glutamic acid, was obtained.

Examples of parent strains which can be used to derive the L-glutamic acid-producing bacteria include, but are not limited to, strains which are deficient in α-ketoglutarate dehydrogenase activity, or strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains which have been modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of strains which have been modified so that expression of the citrate synthetase gene and/or the phosphoenolpyruvate carboxylase gene are reduced, and/or are deficient in α-ketoglutarate dehydrogenase activity include those disclosed in EP1078989A, EP955368A, and EP952221A.

Examples of parent strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881).

*E. coli* W3110sucA::Km$^R$ is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FERM P-12379, which additionally has a low L-glutamic acid decomposing ability (U.S. Pat. No. 5,393,671), AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) may be used (EP 488-424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) which is deficient in tryptophanyl-tRNA synthetase encoded by the mutant trpS gene (U.S. Pat. No. 5,756,345), *E. coli* SV164 (pGH5) having a serA allele encoding phosphoglycerate dehydrogenase which is not subject to feedback inhibition by serine and a trpE allele encoding anthranilate synthase which is not subject to feedback inhibition by tryptophan (U.S. Pat. No. 6,180,373), *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO9708333, U.S. Pat. No. 6,319,696), and the like. L-tryptophan-producing bacteria belonging to the genus *Escherichia* which have enhanced activity of the protein encoded by the yedA or yddG genes may also be used (U.S. patent applications 2003/0148473 A1 and 2003/0157667 A1).

Examples of parent strains which can be used to derive the L-tryptophan-producing bacteria also include strains in which one or more activities are enhanced of the following enzymes: anthranilate synthase (trpE), phosphoglycerate dehydrogenase (serA), and tryptophan synthase (trpAB). The anthranilate synthase and phosphoglycerate dehydrogenase are both subject to feedback inhibition by L-tryptophan and L-serine, therefore a mutation desensitizing the feedback inhibition may be introduced into these enzymes. Specific examples of strains having such a mutation include *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria also include strains which have been transformed with the tryptophan operon containing a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). Tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains which can be used to derive L-proline-producing bacteria include, but are not limited to, strains belonging to the genus Escherichia, such as E. coli 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes include the proB gene coding for glutamate kinase which is desensitized to feedback inhibition by L-proline (DE Patent 3127361). In addition, the bacterium may be improved by enhancing the expression of one or more genes coding for proteins responsible for secreting L-amino acids from the bacterial cell. Such genes are exemplified by the b2682 and b2683 genes (ygaZH genes) (EP1239041 A2).

Examples of bacteria belonging to the genus Escherichia, which have an activity to produce L-proline include the following E. coli strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains which can be used to derive L-arginine-producing bacteria include, but are not limited to, strains belonging to the genus Escherichia, such as E. coli strain 237 (VKPM B-7925) (U.S. Patent Application 2002/058315 A1) and derivatives thereof harboring mutant N-acetylglutamate synthase (Russian Patent Application No. 2001112869), E. coli strain 382 (VKPM B-7926) (EP1170358A1), an arginine-producing strain transformed with the argA gene encoding N-acetylglutamate synthetase (EP1170361A1), and the like.

Examples of parent strains which can be used to derive L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), carbamoyl phosphate synthetase (carAB), and so forth.

L-Valine-Producing Bacteria

Example of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon responsible for attenuation so that the produced L-valine cannot attenuate expression of the operon. Furthermore, the ilvA gene in the operon is desirably disrupted so that threonine deaminase activity is decreased.

Examples of parent strains which can be used to derive L-valine-producing bacteria also include mutants of aminoacyl t-RNA synthetase (U.S. Pat. No. 5,658,766). For example, E. coli VL1970, which has a mutation in the ileS gene encoding isoleucine tRNA synthetase, can be used. E. coli VL1970 has been deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid by cultivating the bacterium in a culture medium to produce and secrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

The chosen culture medium may be either a synthetic or natural medium, so long as it includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganisms can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as by shaking and/or stirring with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated rspAB Operon

1. Deletion of the rspAB Operon.

The rspAB operon was deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers P1 (SEQ ID NO: 5) and P2 (SEQ ID NO: 6), which are complementary to both the region adjacent to the rspAB operon and the gene conferring antibiotic resistance in the template plasmid, were constructed. The plasmid pACYC184 (NBL Gene Sciences Ltd., UK) (GenBank/EMBL accession number X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1152 bp PCR product (FIG. 1) was obtained and purified in agarose gel and used for electroporation of E. coli MG1655 (ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, U.S.A.).

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 hours and were then plated onto L-agar containing chloramphenicol (30 µg/ml) and grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the rspAB Operon Deletion by PCR.

Figure 2:
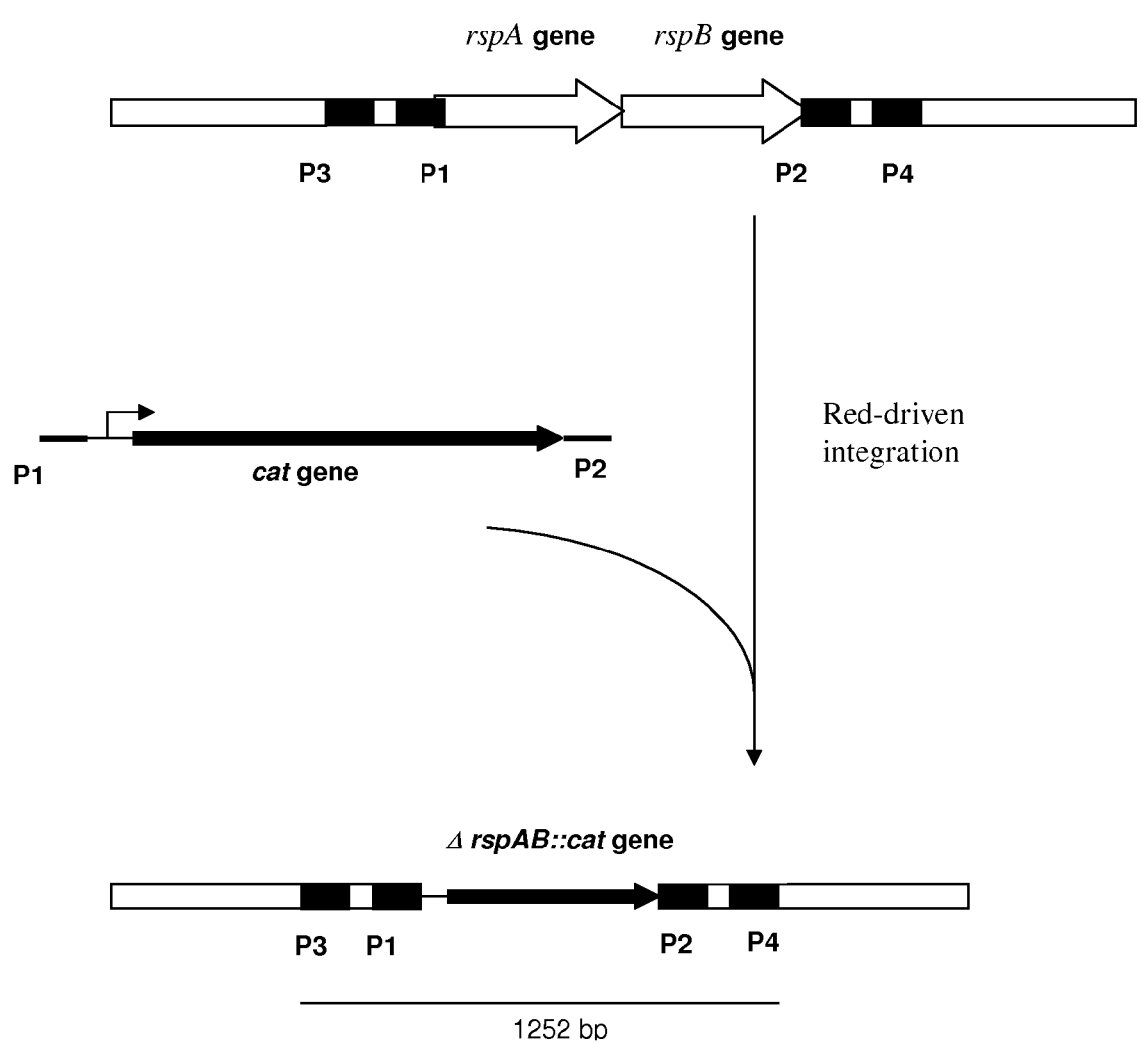
FIG. 2 shows the construction of the chromosomal DNA fragment comprising the inactivated rspAB operon.

The mutants in which the rspAB operon is deleted and are marked with the Cm resistance gene were verified by PCR. Locus-specific primers P3 (SEQ ID NO: 7) and P4 (SEQ ID NO: 8) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained using the parental rspAB$^+$ strain MG1655 as the template, is 2418 bp in length. The PCR product obtained using the mutant strain as the template is 1252 nucleotides in length (FIG. 2). The mutant strain was named MG1655 ΔrspAB::cat.

Example 2

Production of L-Threonine by E. coli Strain B-3996-ΔrspAB

To test the effect of inactivation of the rspAB operon on threonine production, DNA fragments from the chromosome of the above-described E. coli MG1655 ΔrspAB::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain the strain B-3996-ΔrspAB. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1 Dorozhny proezd, 1) under the accession number VKPM B-3996.

Both E. coli B-3996 and B-3996-ΔrspAB, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium was determined by paper chromatography using the following mobile phase:butanol:acetic acid:water=4:1:1 (v/v). A solution of 2% ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results of 8 independent test tube fermentations are shown in Table 1. As follows from Table 1, B-3996-ΔrspAB caused accumulation of a higher amount of L-threonine, as compared with B-3996.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. CaCO₃ was sterilized by dry-heat at 180° C. for 2 hours. The pH was adjusted to 7.0.

TABLE 1

| Strain | OD$_{540}$ | Amount of L-threonine, g/l |
|---|---|---|
| B-3996 | 25.0 ± 1.1 | 29.0 ± 0.4 |
| B-3996-ΔrspAB | 25.9 ± 1.0 | 29.5 ± 1.1 |

Example 3

Production of L-Lysine by *E. coli* AJ11442-ΔrspAB

To test the effect of inactivation of the rspAB operon on lysine production, DNA fragments from the chromosome of the above-described *E. coli* strain MG1655 ΔrspAB::cat can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain the AJ11442-ΔrspAB strain. The strain AJ14442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both *E. coli* strains, AJ11442 and AJ11442-ΔrspAB, can be cultured in L-medium containing streptomycin (20 mg/l) at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| Glucose | 40 |
|---|---|
| (NH₄)₂SO₄ | 24 |
| K₂HPO₄ | 1.0 |
| MgSO₄•7H₂O | 1.0 |
| FeSO₄•7H₂O | 0.01 |
| MnSO₄•5H₂O | 0.01 |
| Yeast extract | 2.0 |

The pH is adjusted to 7.0 by KOH and the medium is autoclaved at 115° C. for 10 min. Glucose and MgSO₄.7H₂O are sterilized separately. CaCO₃ is dry-heat sterilized at 180° C. for 2 hours and added to the medium for a final concentration of 30 μl.

Example 4

Production of L-Cysteine by *E. coli* JM15(ydeD)-ΔrspAB

To test the effect of inactivation of the rspAB operon on L-cysteine production, DNA fragments from the chromosome of the above-described *E. coli* MG1655 ΔrspAB::cat can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-ΔrspAB.

*E. coli* JM15(ydeD) is a derivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC# 5042) can be obtained from The Coli Genetic Stock Collection at the *E. coli* Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 5

Production of L-Leucine by *E. coli* 57-ΔrspAB

To test the effect of inactivation of the rspAB operon on L-leucine production, DNA fragments from the chromosome of the above-described *E. coli* strain MG1655 ΔrspAB::cat can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-pMW-ΔrspAB. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains, 57 and 57-ΔrspAB, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1).

The composition of the fermentation medium (g/l) (pH 7.2) is as follows:

| Glucose | 60.0 |
|---|---|
| (NH₄)₂SO₄ | 25.0 |
| K₂HPO₄ | 2.0 |
| MgSO₄•7H₂O | 1.0 |
| Thiamine | 0.01 |
| CaCO₃ | 25.0 |

Glucose and CaCO₃ are sterilized separately.

Example 6

Production of L-Histidine by E. coli 80-ΔrspAB

To test the effect of inactivation of the rspAB operon on L-histidine production, DNA fragments from the chromosome of the above-described E. coli MG1655 ΔrspAB::cat can be transferred to the histidine-producing E. coli strain 80 by P1 transduction (Miller, J. H. Experiments in Molecular Genetics, Cold Spring Harbor Lab. Press, 1972, Plainview, N.Y.) to obtain strain 80-ΔrspAB. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both E. coli strains, 80 and 80-ΔrspAB, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 7

Production of L-Glutamate by E. coli VL334thrC⁺-ΔrspAB

To test the effect of inactivation of the rspAB operon on L-glutamate production, DNA fragments from the chromosome of the above-described E. coli strain MG1655 ΔrspAB::cat can be transferred to the E. coli L-glutamate-producing strain VL334thrC⁺ (EP 1172433) by P1 transduction (Miller, J. H. Experiments in Molecular Genetics, Cold Spring Harbor Lab. Press, 1972, Plainview, N.Y.) to obtain the strain VL334thrC⁺-ΔrspAB The strain VL334thrC⁺ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC⁺ and VL334thrC⁺-ΔrspAB, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), $KH_2PO_4$ (2 g/l), $MgSO_4$ (1 g/l), thiamine (0.1 mg/ml), L-isoleucine (70 μg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 8

Production of L-Phenylalanine by E. coli AJ12739-ΔrspAB

To test the effect of inactivation of the rspAB operon on L-phenylalanine production, DNA fragments from the chromosome of the above-described E. coli MG1655 ΔrspAB::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain strain AJ12739-ΔrspAB. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Both strains, AJ12739-ΔrspAB and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 9

Production of L-Tryptophan by E. coli SV164 (pGH5)-ΔrspAB

To test the effect of inactivation of the rspAB operon on L-tryptophan production, DNA fragments from the chromosome of the above-described E. coli strain MG1655 ΔrspAB::

cat can be transferred to the tryptophan-producing *E. coli* strain SV164 (pGH5) by P1 transduction (Miller, J. H. Experiments in Molecular Genetics, Cold Spring Harbor Lab. Press, 1972, Plainview, N.Y.) to obtain the strain SV164 (pGH5)-ΔrspAB. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143.

Both strains, SV164(pGH5)-ΔrspAB and SV164(pGH5), can each be cultivated with shaking at 37° C. for 18 hours in 3 ml of nutrient broth supplemented with tetracycline (20 mg/l, marker of pGH5 plasmid). The obtained cultures (0.3 ml each) can be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 2, but should be sterilized in separate groups (A, B, C, D, E, F, and H), as shown, to avoid adverse interactions during sterilization.

TABLE 2

| Groups | Component | Final concentration, g/l |
|---|---|---|
| A | $KH_2PO_4$ | 1.5 |
|   | NaCl | 0.5 |
|   | $(NH_4)_2SO_4$ | 1.5 |
|   | L-Methionine | 0.05 |
|   | L-Phenylalanine | 0.1 |
|   | L-Tyrosine | 0.1 |
|   | Mameno (total N) | 0.07 |
| B | Glucose | 40.0 |
|   | $MgSO_4 \cdot 7H_2O$ | 0.3 |
| C | $CaCl_2$ | 0.011 |
| D | $FeSO_4 \cdot 7H_2O$ | 0.075 |
|   | Sodium citrate | 1.0 |
| E | $Na_2MoO_4 \cdot 2H_2O$ | 0.00015 |
|   | $H_3BO_3$ | 0.0025 |
|   | $CoCl_2 \cdot 6H_2O$ | 0.00007 |
|   | $CuSO_4 \cdot 5H_2O$ | 0.00025 |
|   | $MnCl_2 \cdot 4H_2O$ | 0.0016 |
|   | $ZnSO_4 \cdot 7H_2O$ | 0.0003 |
| F | Thiamine HCl | 0.005 |
| G | $CaCO_3$ | 30.0 |
| H | Pyridoxine | 0.03 |

Group A had pH 7.1 adjusted by $NH_4OH$. Each group is sterilized separately, chilled, and then mixed together.

Example 10

Production of L-Proline by *E. coli* 702ilvA-ΔrspAB

To test the effect of inactivation of the rspAB operon on L-proline production, DNA fragments from the chromosome of the above-described *E. coli* strain MG1655 ΔrspAB::cat can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain the strain 702ilvA-ΔrspAB. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both *E. coli* strains, 702ilvA and 702ilvA-ΔrspAB, can be grown for 18-24 hours at 37° C. on L-agar plates. Then, these strains can be cultivated under the same conditions as in Example 8.

Example 11

Production of L-Arginine by *E. coli* 382-ΔrspAB

To test the effect of inactivation of the rspAB operon on L-arginine production, DNA fragments from the chromosome of the above-described *E. coli* strain MG1655 ΔrspAB::cat can be transferred to the arginine-producing *E. coli* strain 382 by P1 transduction (Miller, J. H. Experiments in Molecular Genetics, Cold Spring Harbor Lab. Press, 1972, Plainview, N.Y.) to obtain strain 382-ΔrspAB. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382-ΔrspAB and 382, can be separately cultivated with shaking at 37° C. for 18 hours in 3 ml of nutrient broth, and 0.3 ml of the obtained cultures can be inoculated into 2 ml of a fermentation medium in 20×200-mm test tubes and cultivated at 32° C. for 48 hours on a rotary shaker.

After the cultivation, the amount of L-arginine which accumulates in the medium can be determined by paper chromatography using the following mobile phase:butanol:acetic acid:water=4:1:1 (v/v). A solution of ninhydrin (2%) in acetone can be used as a visualizing reagent. A spot containing L-arginine can be cut out, L-arginine was eluted with 0.5% water solution of $CdCl_2$, and the amount of L-arginine can be estimated spectrophotometrically at 540 nm.

The composition of the fermentation medium (g/l) is as follows:

| Glucose | 48.0 |
|---|---|
| $(NH4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of an L-amino acid by a bacterium of the Enterobacteriaceae family can be enhanced.

The invention claimed is:

1. A method for producing an L-amino acid comprising:

I) cultivating an L-amino acid-producing *Escherichia coli* bacterium in a medium, and II) collecting said L-amino acid from the medium, wherein said bacterium has been modified to attenuate expression of the rspAB operon by a method selected from the group consisting of:

A) deleting a part of the rspAB operon,

B) shifting the reading frame of the rspAB operon,

C) introducing one or more missense and/or nonsense mutations into the rspAB operon, D) modifying a region that is adjacent to the rspAB operon which controls gene expression, and E) combinations thereof; and wherein the rspAB operon comprises the rspA and rspB genes, and wherein the rspA and rspB genes encode proteins having at least 95% homology to the amino acid sequence of SEQ ID NO: 2 and SEQ ID NO: 4, respectively.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

5. The method according to claim 1, wherein the rspA and rspB genes encode proteins consisting of the amino acid sequence of SEQ ID NO: 2 and SEQ ID NO: 4, respectively.

* * * * *

SEQUENCE LISTING

<160> NUMBER OF SEQ ID NOS: 8

<210> SEQ ID NO 1
<211> LENGTH: 1215
<212> TYPE: DNA
<213> ORGANISM: Escherichia coli
<220> FEATURE:
<221> NAME/KEY: CDS
<222> LOCATION: (1)..(1215)

<400> SEQUENCE: 1

| | | | | | | | | | | | | | | | | |
|---|---|---|---|---|---|---|---|---|---|---|---|---|---|---|---|---|
| atg | aag | atc | gta | aag | gct | gaa | gtt | ttt | gtt | acc | tgt | ccg | ggg | cgt | aat | 48 |
| Met | Lys | Ile | Val | Lys | Ala | Glu | Val | Phe | Val | Thr | Cys | Pro | Gly | Arg | Asn | |
| 1 | | | | 5 | | | | | 10 | | | | | 15 | | |

| ttc | gtc | aca | tta | aaa | atc | acc | act | gag | gac | ggt | att | acg | ggc | ctt | ggg | 96 |
|---|---|---|---|---|---|---|---|---|---|---|---|---|---|---|---|---|
| Phe | Val | Thr | Leu | Lys | Ile | Thr | Thr | Glu | Asp | Gly | Ile | Thr | Gly | Leu | Gly | |
| | | | 20 | | | | | 25 | | | | | 30 | | | |

| gat | gcc | acc | ctc | aat | gga | cgt | gag | ctt | tcc | gtg | gcc | tct | tat | ttg | cag | 144 |
|---|---|---|---|---|---|---|---|---|---|---|---|---|---|---|---|---|
| Asp | Ala | Thr | Leu | Asn | Gly | Arg | Glu | Leu | Ser | Val | Ala | Ser | Tyr | Leu | Gln | |
| | | 35 | | | | | 40 | | | | | 45 | | | | |

| gat | cac | ctt | tgt | ccg | cag | ctt | att | ggt | cgc | gat | gcg | cac | cgt | atc | gaa | 192 |
|---|---|---|---|---|---|---|---|---|---|---|---|---|---|---|---|---|
| Asp | His | Leu | Cys | Pro | Gln | Leu | Ile | Gly | Arg | Asp | Ala | His | Arg | Ile | Glu | |
| 50 | | | | | 55 | | | | | 60 | | | | | | |

| gat | atc | tgg | cag | ttt | ttc | tat | aaa | ggt | gct | tac | tgg | cgt | cgc | ggt | ccg | 240 |
|---|---|---|---|---|---|---|---|---|---|---|---|---|---|---|---|---|
| Asp | Ile | Trp | Gln | Phe | Phe | Tyr | Lys | Gly | Ala | Tyr | Trp | Arg | Arg | Gly | Pro | |
| 65 | | | | | 70 | | | | | 75 | | | | | 80 | |

| gtt | acg | atg | tcg | gcc | att | tca | gcg | gtt | gat | atg | gcg | ctg | tgg | gat | att | 288 |
|---|---|---|---|---|---|---|---|---|---|---|---|---|---|---|---|---|
| Val | Thr | Met | Ser | Ala | Ile | Ser | Ala | Val | Asp | Met | Ala | Leu | Trp | Asp | Ile | |
| | | | | 85 | | | | | 90 | | | | | 95 | | |

| aaa | gcc | aaa | gct | gcc | aac | atg | ccg | ctt | tac | cag | tta | ctc | ggc | ggc | gcg | 336 |
|---|---|---|---|---|---|---|---|---|---|---|---|---|---|---|---|---|
| Lys | Ala | Lys | Ala | Ala | Asn | Met | Pro | Leu | Tyr | Gln | Leu | Leu | Gly | Gly | Ala | |
| | | | | 100 | | | | | 105 | | | | | 110 | | |

| tct | cgt | gaa | ggg | gtg | atg | gtt | tat | tgc | cat | acc | acc | ggt | cac | agt | att | 384 |
|---|---|---|---|---|---|---|---|---|---|---|---|---|---|---|---|---|
| Ser | Arg | Glu | Gly | Val | Met | Val | Tyr | Cys | His | Thr | Thr | Gly | His | Ser | Ile | |
| | | | 115 | | | | | 120 | | | | | 125 | | | |

| gat | gaa | gct | ctg | gat | gat | tat | gcc | cgt | cat | caa | gag | ctt | gga | ttc | aaa | 432 |
|---|---|---|---|---|---|---|---|---|---|---|---|---|---|---|---|---|
| Asp | Glu | Ala | Leu | Asp | Asp | Tyr | Ala | Arg | His | Gln | Glu | Leu | Gly | Phe | Lys | |
| | | 130 | | | | | 135 | | | | | 140 | | | | |

| gcc | atc | cgc | gtg | cag | tgc | gga | atc | cct | ggt | atg | aaa | acc | acc | tac | ggc | 480 |
|---|---|---|---|---|---|---|---|---|---|---|---|---|---|---|---|---|
| Ala | Ile | Arg | Val | Gln | Cys | Gly | Ile | Pro | Gly | Met | Lys | Thr | Thr | Tyr | Gly | |
| 145 | | | | | 150 | | | | | 155 | | | | | 160 | |

| atg | tcg | aaa | ggt | aaa | ggt | ctg | gct | tat | gaa | ccc | gca | acc | aaa | gga | cag | 528 |
|---|---|---|---|---|---|---|---|---|---|---|---|---|---|---|---|---|
| Met | Ser | Lys | Gly | Lys | Gly | Leu | Ala | Tyr | Glu | Pro | Ala | Thr | Lys | Gly | Gln | |
| | | | | 165 | | | | | 170 | | | | | 175 | | |

| tgg | ccg | gaa | gag | cag | ctg | tgg | tcg | acg | gag | aaa | tac | ctc | gat | ttc | atg | 576 |
|---|---|---|---|---|---|---|---|---|---|---|---|---|---|---|---|---|
| Trp | Pro | Glu | Glu | Gln | Leu | Trp | Ser | Thr | Glu | Lys | Tyr | Leu | Asp | Phe | Met | |
| | | | | 180 | | | | | 185 | | | | | 190 | | |

| ccg | aaa | ttg | ttt | gac | gcg | gta | cgt | aac | aag | ttt | ggt | ttt | aat | gaa | cat | 624 |
|---|---|---|---|---|---|---|---|---|---|---|---|---|---|---|---|---|
| Pro | Lys | Leu | Phe | Asp | Ala | Val | Arg | Asn | Lys | Phe | Gly | Phe | Asn | Glu | His | |
| | | | 195 | | | | | 200 | | | | | 205 | | | |

| ttg | ctg | cat | gac | atg | cac | cat | cgc | tta | acg | cct | att | gaa | gcg | gcg | cgc | 672 |
|---|---|---|---|---|---|---|---|---|---|---|---|---|---|---|---|---|
| Leu | Leu | His | Asp | Met | His | His | Arg | Leu | Thr | Pro | Ile | Glu | Ala | Ala | Arg | |
| | | 210 | | | | | 215 | | | | | 220 | | | | |

| ttt | ggt | aaa | agc | att | gaa | gat | tat | cgc | atg | ttc | tgg | atg | gaa | gac | ccg | 720 |
|---|---|---|---|---|---|---|---|---|---|---|---|---|---|---|---|---|
| Phe | Gly | Lys | Ser | Ile | Glu | Asp | Tyr | Arg | Met | Phe | Trp | Met | Glu | Asp | Pro | |
| 225 | | | | | 230 | | | | | 235 | | | | | 240 | |

| acg | cct | gcg | gaa | aac | cag | gaa | tgc | ttc | cgt | ctc | att | cgc | caa | cat | acc | 768 |
|---|---|---|---|---|---|---|---|---|---|---|---|---|---|---|---|---|
| Thr | Pro | Ala | Glu | Asn | Gln | Glu | Cys | Phe | Arg | Leu | Ile | Arg | Gln | His | Thr | |
| | | | | 245 | | | | | 250 | | | | | 255 | | |

```
gtc aca ccc atc gca gtg ggt gaa gtc ttc aac agc atc tgg gac tgc      816
Val Thr Pro Ile Ala Val Gly Glu Val Phe Asn Ser Ile Trp Asp Cys
        260                 265                 270 aaa caa ctg att gaa gag caa ctc atc gat tat atc cgc acc acg ctg      864
Lys Gln Leu Ile Glu Glu Gln Leu Ile Asp Tyr Ile Arg Thr Thr Leu
    275                 280                 285 acc cat gca ggc gga att acc ggt atg cgc cgg att gcc gat ttt gct      912
Thr His Ala Gly Gly Ile Thr Gly Met Arg Arg Ile Ala Asp Phe Ala
290                 295                 300 tcg ctg tat cag gta cgt act ggc tca cac ggt cct tcc gat ttg tca      960
Ser Leu Tyr Gln Val Arg Thr Gly Ser His Gly Pro Ser Asp Leu Ser
305                 310                 315                 320 cca gtc tgc atg gct gcg gcg ctg cac ttt gat ctg tgg gtc ccc aat     1008
Pro Val Cys Met Ala Ala Ala Leu His Phe Asp Leu Trp Val Pro Asn
                325                 330                 335 ttc ggt gtc cag gaa tac atg ggt tat tcc gaa caa atg ctc gaa gtc     1056
Phe Gly Val Gln Glu Tyr Met Gly Tyr Ser Glu Gln Met Leu Glu Val
            340                 345                 350 ttc ccg cac aac tgg act ttc gat aac ggc tat atg cat ccg gga gac     1104
Phe Pro His Asn Trp Thr Phe Asp Asn Gly Tyr Met His Pro Gly Asp
        355                 360                 365 aaa ccg ggt ctt ggt atc gaa ttc gat gaa aag ctg gcg gcg aaa tat     1152
Lys Pro Gly Leu Gly Ile Glu Phe Asp Glu Lys Leu Ala Ala Lys Tyr
    370                 375                 380 ccc tat gaa cct gct tat cta cca gtc gca cgt ctg gaa gat ggc acg     1200
Pro Tyr Glu Pro Ala Tyr Leu Pro Val Ala Arg Leu Glu Asp Gly Thr
385                 390                 395                 400 ctg tgg aac tgg taa                                                  1215
Leu Trp Asn Trp <210> SEQ ID NO 2
<211> LENGTH: 404
<212> TYPE: PRT
<213> ORGANISM: Escherichia coli

<400> SEQUENCE: 2

Met Lys Ile Val Lys Ala Glu Val Phe Val Thr Cys Pro Gly Arg Asn
1               5                   10                  15

Phe Val Thr Leu Lys Ile Thr Thr Glu Asp Gly Ile Thr Gly Leu Gly
            20                  25                  30

Asp Ala Thr Leu Asn Gly Arg Glu Leu Ser Val Ala Ser Tyr Leu Gln
        35                  40                  45

Asp His Leu Cys Pro Gln Leu Ile Gly Arg Asp Ala His Arg Ile Glu
    50                  55                  60

Asp Ile Trp Gln Phe Phe Tyr Lys Gly Ala Tyr Trp Arg Arg Gly Pro
65                  70                  75                  80

Val Thr Met Ser Ala Ile Ser Ala Val Asp Met Ala Leu Trp Asp Ile
                85                  90                  95

Lys Ala Lys Ala Ala Asn Met Pro Leu Tyr Gln Leu Leu Gly Gly Ala
            100                 105                 110

Ser Arg Glu Gly Val Met Val Tyr Cys His Thr Thr Gly His Ser Ile
        115                 120                 125

Asp Glu Ala Leu Asp Asp Tyr Ala Arg His Gln Glu Leu Gly Phe Lys
    130                 135                 140

Ala Ile Arg Val Gln Cys Gly Ile Pro Gly Met Lys Thr Thr Tyr Gly
145                 150                 155                 160

Met Ser Lys Gly Lys Gly Leu Ala Tyr Glu Pro Ala Thr Lys Gly Gln
                165                 170                 175
```

```
Trp Pro Glu Glu Gln Leu Trp Ser Thr Glu Lys Tyr Leu Asp Phe Met
                180                 185                 190

Pro Lys Leu Phe Asp Ala Val Arg Asn Lys Phe Gly Phe Asn Glu His
            195                 200                 205

Leu Leu His Asp Met His His Arg Leu Thr Pro Ile Glu Ala Ala Arg
        210                 215                 220

Phe Gly Lys Ser Ile Glu Asp Tyr Arg Met Phe Trp Met Glu Asp Pro
225                 230                 235                 240

Thr Pro Ala Glu Asn Gln Glu Cys Phe Arg Leu Ile Arg Gln His Thr
                245                 250                 255

Val Thr Pro Ile Ala Val Gly Glu Val Phe Asn Ser Ile Trp Asp Cys
            260                 265                 270

Lys Gln Leu Ile Glu Glu Gln Leu Ile Asp Tyr Ile Arg Thr Thr Leu
        275                 280                 285

Thr His Ala Gly Gly Ile Thr Gly Met Arg Arg Ile Ala Asp Phe Ala
290                 295                 300

Ser Leu Tyr Gln Val Arg Thr Gly Ser His Gly Pro Ser Asp Leu Ser
305                 310                 315                 320

Pro Val Cys Met Ala Ala Ala Leu His Phe Asp Leu Trp Val Pro Asn
                325                 330                 335

Phe Gly Val Gln Glu Tyr Met Gly Tyr Ser Glu Gln Met Leu Glu Val
            340                 345                 350

Phe Pro His Asn Trp Thr Phe Asp Asn Gly Tyr Met His Pro Gly Asp
        355                 360                 365

Lys Pro Gly Leu Gly Ile Glu Phe Asp Glu Lys Leu Ala Ala Lys Tyr
370                 375                 380

Pro Tyr Glu Pro Ala Tyr Leu Pro Val Ala Arg Leu Glu Asp Gly Thr
385                 390                 395                 400

Leu Trp Asn Trp

<210> SEQ ID NO 3
<211> LENGTH: 1020
<212> TYPE: DNA
<213> ORGANISM: Escherichia coli
<220> FEATURE:
<221> NAME/KEY: CDS
<222> LOCATION: (1)..(1020)

<400> SEQUENCE: 3 atg aaa agc ata tta att gaa aaa ccg aat caa ctg gcg att gtc gaa    48
Met Lys Ser Ile Leu Ile Glu Lys Pro Asn Gln Leu Ala Ile Val Glu
1               5                   10                  15 cgt gaa ata ccc acc ccg tca gcg ggt gaa gta cga gta aaa gtg aaa    96
Arg Glu Ile Pro Thr Pro Ser Ala Gly Glu Val Arg Val Lys Val Lys
                20                  25                  30 ctt gcc gga att tgt ggt tca gat agc cat att tat cgt ggg cat aat   144
Leu Ala Gly Ile Cys Gly Ser Asp Ser His Ile Tyr Arg Gly His Asn
            35                  40                  45 cct ttt gcg aaa tat ccg cgc gtc att ggt cat gaa ttc ttt ggc gtc   192
Pro Phe Ala Lys Tyr Pro Arg Val Ile Gly His Glu Phe Phe Gly Val
        50                  55                  60 att gat gca gtg ggt gaa ggc gtg gaa agc gcc aga gtc ggt gaa cgt   240
Ile Asp Ala Val Gly Glu Gly Val Glu Ser Ala Arg Val Gly Glu Arg
65                  70                  75                  80 gtt gct gtc gat ccg gtg gtc agc tgt ggg cat tgc tat ccg tgc tct   288
Val Ala Val Asp Pro Val Val Ser Cys Gly His Cys Tyr Pro Cys Ser
                85                  90                  95
```

```
ata ggt aaa ccg aac gtt tgt acg aca ctg gct gta tta ggt gtg cac      336
Ile Gly Lys Pro Asn Val Cys Thr Thr Leu Ala Val Leu Gly Val His
        100                 105                 110 gct gac ggt ggt ttc agt gaa tat gcc gtg gtt ccg gca aaa aat gcg      384
Ala Asp Gly Gly Phe Ser Glu Tyr Ala Val Val Pro Ala Lys Asn Ala
            115                 120                 125 tgg aaa att cct gaa gca gtg gcc gat caa tat gcg gta atg atc gaa      432
Trp Lys Ile Pro Glu Ala Val Ala Asp Gln Tyr Ala Val Met Ile Glu
    130                 135                 140 cct ttt acc att gcg gct aac gta acc gga cat ggt caa ccg act gaa      480
Pro Phe Thr Ile Ala Ala Asn Val Thr Gly His Gly Gln Pro Thr Glu
145                 150                 155                 160 aat gat acc gtt ctg gtt tat ggt gcc ggt cca atc ggc ctg acg atc      528
Asn Asp Thr Val Leu Val Tyr Gly Ala Gly Pro Ile Gly Leu Thr Ile
                165                 170                 175 gtt cag gta tta aaa ggc gtc tat aac gtt aaa aat gtg att gtt gcc      576
Val Gln Val Leu Lys Gly Val Tyr Asn Val Lys Asn Val Ile Val Ala
            180                 185                 190 gat cgc att gat gaa cga ctg gaa aaa gcg aaa gag agc ggg gct gac      624
Asp Arg Ile Asp Glu Arg Leu Glu Lys Ala Lys Glu Ser Gly Ala Asp
    195                 200                 205 tgg gcg att aat aac agc cag aca ccg ctt ggc gag att ttc act gaa      672
Trp Ala Ile Asn Asn Ser Gln Thr Pro Leu Gly Glu Ile Phe Thr Glu
210                 215                 220 aaa ggc atc aag ccg aca tta att atc gat gcg gct tgt cat cct tct      720
Lys Gly Ile Lys Pro Thr Leu Ile Ile Asp Ala Ala Cys His Pro Ser
225                 230                 235                 240 atc ctg aaa gag gcc gta acg ctg gct tct cca gcg gca cgt att gta      768
Ile Leu Lys Glu Ala Val Thr Leu Ala Ser Pro Ala Ala Arg Ile Val
                245                 250                 255 ttg atg ggg ttc tcc agt gaa ccg tct gaa gtg att cag caa gga att      816
Leu Met Gly Phe Ser Ser Glu Pro Ser Glu Val Ile Gln Gln Gly Ile
            260                 265                 270 acc gga aaa gaa ctc tct att ttc tct tca cgc tta aat gca aat aaa      864
Thr Gly Lys Glu Leu Ser Ile Phe Ser Ser Arg Leu Asn Ala Asn Lys
    275                 280                 285 ttc ccg atc gtt atc gac tgg tta agt aaa ggg tta att aaa cca gaa      912
Phe Pro Ile Val Ile Asp Trp Leu Ser Lys Gly Leu Ile Lys Pro Glu
290                 295                 300 aaa tta att acc cat acg ttt gat ttc cag cat gtt gct gat gcc att      960
Lys Leu Ile Thr His Thr Phe Asp Phe Gln His Val Ala Asp Ala Ile
305                 310                 315                 320 agt tta ttt gaa cag gat caa aaa cat tgc tgc aaa gtc tta ctc act     1008
Ser Leu Phe Glu Gln Asp Gln Lys His Cys Cys Lys Val Leu Leu Thr
                325                 330                 335 ttt tct gaa taa                                                     1020
Phe Ser Glu <210> SEQ ID NO 4
<211> LENGTH: 339
<212> TYPE: PRT
<213> ORGANISM: Escherichia coli

<400> SEQUENCE: 4

Met Lys Ser Ile Leu Ile Glu Lys Pro Asn Gln Leu Ala Ile Val Glu
1               5                   10                  15

Arg Glu Ile Pro Thr Pro Ser Ala Gly Glu Val Arg Val Lys Val Lys
            20                  25                  30

Leu Ala Gly Ile Cys Gly Ser Asp Ser His Ile Tyr Arg Gly His Asn
```

```
                35                  40                  45
Pro Phe Ala Lys Tyr Pro Arg Val Ile Gly His Glu Phe Phe Gly Val
 50                  55                  60
Ile Asp Ala Val Gly Glu Gly Val Glu Ser Ala Arg Val Gly Glu Arg
 65                  70                  75                  80
Val Ala Val Asp Pro Val Val Ser Cys Gly His Cys Tyr Pro Cys Ser
                 85                  90                  95
Ile Gly Lys Pro Asn Val Cys Thr Thr Leu Ala Val Leu Gly Val His
                100                 105                 110
Ala Asp Gly Gly Phe Ser Glu Tyr Ala Val Val Pro Ala Lys Asn Ala
                115                 120                 125
Trp Lys Ile Pro Glu Ala Val Ala Asp Gln Tyr Ala Val Met Ile Glu
130                 135                 140
Pro Phe Thr Ile Ala Ala Asn Val Thr Gly His Gly Gln Pro Thr Glu
145                 150                 155                 160
Asn Asp Thr Val Leu Val Tyr Gly Ala Gly Pro Ile Gly Leu Thr Ile
                165                 170                 175
Val Gln Val Leu Lys Gly Val Tyr Asn Val Lys Asn Val Ile Val Ala
                180                 185                 190
Asp Arg Ile Asp Glu Arg Leu Glu Lys Ala Lys Glu Ser Gly Ala Asp
                195                 200                 205
Trp Ala Ile Asn Asn Ser Gln Thr Pro Leu Gly Glu Ile Phe Thr Glu
210                 215                 220
Lys Gly Ile Lys Pro Thr Leu Ile Ile Asp Ala Ala Cys His Pro Ser
225                 230                 235                 240
Ile Leu Lys Glu Ala Val Thr Leu Ala Ser Pro Ala Ala Arg Ile Val
                245                 250                 255
Leu Met Gly Phe Ser Ser Glu Pro Ser Glu Val Ile Gln Gln Gly Ile
                260                 265                 270
Thr Gly Lys Glu Leu Ser Ile Phe Ser Ser Arg Leu Asn Ala Asn Lys
                275                 280                 285
Phe Pro Ile Val Ile Asp Trp Leu Ser Lys Gly Leu Ile Lys Pro Glu
290                 295                 300
Lys Leu Ile Thr His Thr Phe Asp Phe Gln His Val Ala Asp Ala Ile
305                 310                 315                 320
Ser Leu Phe Glu Gln Asp Gln Lys His Cys Cys Lys Val Leu Leu Thr
                325                 330                 335
Phe Ser Glu

<210> SEQ ID NO 5
<211> LENGTH: 57
<212> TYPE: DNA
<213> ORGANISM: Artificial
<220> FEATURE:
<223> OTHER INFORMATION: primer P1

<400> SEQUENCE: 5
ttcatgcatc acgacaagcg atgcaaggaa tcgaacttaa gggcaccaat aactgcc      57

<210> SEQ ID NO 6
<211> LENGTH: 57
<212> TYPE: DNA
<213> ORGANISM: Artificial
<220> FEATURE:
<223> OTHER INFORMATION: primer P2

<400> SEQUENCE: 6
```

```
ggtaagatgc gtactactta ctcgccgtta ttggtatagt aagccagtat acactcc        57

<210> SEQ ID NO 7
<211> LENGTH: 21
<212> TYPE: DNA
<213> ORGANISM: Artificial
<220> FEATURE:
<223> OTHER INFORMATION: primer P3

<400> SEQUENCE: 7
tatggtagta gctcagttgc g                                               21

<210> SEQ ID NO 8
<211> LENGTH: 21
<212> TYPE: DNA
<213> ORGANISM: Artificial
<220> FEATURE:
<223> OTHER INFORMATION: primer P4

<400> SEQUENCE: 8
actgctgctt tcaccaaatc c                                               21
```